United States Patent [19]

Kocal et al.

[11] Patent Number: 4,783,566
[45] Date of Patent: Nov. 8, 1988

[54] HYDROCARBON CONVERSION PROCESS

[75] Inventors: Joseph A. Kocal, Gurnee; David C. Martindale, Roselle; Paul J. Kuchar, Hinsdale, all of Ill.

[73] Assignee: UOP Inc., Des Plaines, Ill.

[21] Appl. No.: 90,480

[22] Filed: Aug. 28, 1987

[51] Int. Cl.$^4$ .................... C07C 12/00; C07C 12/02
[52] U.S. Cl. .................... 585/415; 585/413; 585/444; 585/518; 585/466; 208/135; 208/262.1; 208/140
[58] Field of Search .............. 585/413, 415; 208/135, 208/140, 262

[56] References Cited

U.S. PATENT DOCUMENTS

| | | | |
|---|---|---|---|
| 2,180,712 | 11/1939 | Logan | 183/4 |
| 3,594,331 | 7/1971 | Elliott, Jr. | 252/442 |
| 3,756,961 | 9/1973 | Francis et al. | 252/419 |
| 3,775,310 | 11/1973 | Conway et al. | 210/33 |
| 3,933,983 | 1/1976 | Elliott, Jr. | 423/328 |
| 4,456,527 | 6/1984 | Buss et al. | 208/89 |
| 4,480,144 | 10/1984 | Smith | 585/481 |
| 4,542,248 | 9/1985 | Lucien | 585/415 |

FOREIGN PATENT DOCUMENTS

| | | | |
|---|---|---|---|
| 1218348 | 2/1987 | Canada | 253/13 |
| 0107877 | 5/1984 | European Pat. Off. | 585/415 |

Primary Examiner—Curtis R. Davis
Assistant Examiner—Helane Myers
Attorney, Agent, or Firm—Thomas K. McBride; John F. Spears, Jr.; A. Blair Hughes

[57] ABSTRACT

A hydrocarbon conversion process is disclosed which extends the useful life of a regenerable zeolite-containing hydrocarbon conversion catalyst. In one aspect of this process, a hydrocarbon feed containing fluorides is passed through a fluoride removal system which reduces the fluoride concentration of the feed to below 100 ppb. The hydrocarbon feed containing less than 100 ppb fluorine is then converted over a regenerable zeolite-containing hydrocarbon conversion catalyst. The zeolite-containing hydrocarbon conversion catalyst is regenerated with an oxygen-containing gas stream as necessary to burn off carbonaceous deposits on the catalyst so as to return the zeolite catalyst to a high level of activity.

11 Claims, 1 Drawing Sheet

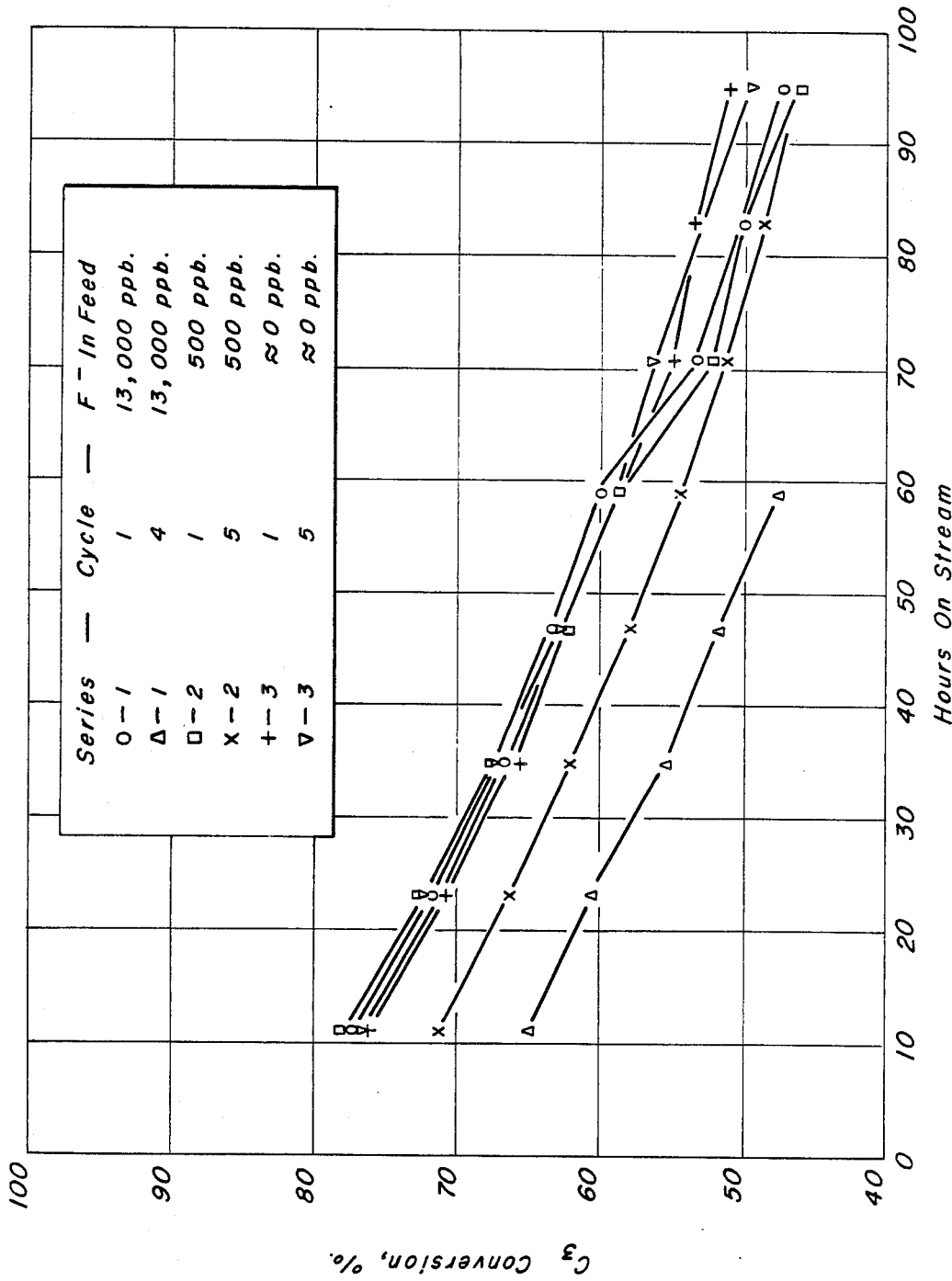

A principal object of the present invention is to provide an improved hydrocarbon conversion process which overcomes prior art zeolite-containing hydrocarbon conversion catalyst stability problems by recognizing the high sensitivity of zeolite catalysts to fluorine compounds by controlling the fluorine concentration of hydrocarbon feeds to such zeolite catalyzed processes to less than 100 ppb. Using such a feed in a process which employs a regenerable zeolite-containing catalyst results in an extension of the useful life of the zeolite-containing catalyst. Accordingly, a broad embodiment of the process of the present invention is directed toward a hydrocarbon conversion process for catalytically converting a hydrocarbon containing feed having a fluorine concentration of below 100 ppb in the presence of a regenerable catalyst comprising a crystalline zeolite at hydrocarbon conversion conditions.

HYDROCARBON CONVERSION PROCESS

BACKGROUND OF THE INVENTION

The present invention relates to an improved hydrocarbon conversion process which utilizes a regenerable zeolite-containing catalyst to process a hydrocarbon feed which has been treated to reduce the fluoride content therein to below 100 ppb.

It is a common practice in the hydrocarbon and petrochemical industry to treat feedstocks, products, and intermediates in order to purify streams or to remove deleterious components from hydrocarbon streams. Hydrocarbon feedstocks and intermediate process streams are often purified to increase process efficiency. That is, it is much more efficient to process reactant hydrocarbons than it is to include refractory hydrocarbons or hydrocarbons which lead to undesirable products in a catalyzed hydrocarbon process. Hydrocarbon reaction products are often purified or otherwise treated to enhance the products value, stability, and so forth.

Additionally, impurities in hydrocarbons being processed in a catalytic system have been recognized as having a negative effect on catalyst stability and conversion. For example, cracking catalysts are poisoned by metals such as nickel, vanadium, and sodium which originate in the hydrocarbon feed to a cracking unit. Treatment of such a feed to remove or passivate such metals is well known to increase the useful life of cracking catalysts. In another example, sulfur accumulation on a reforming catalyst promotes undesirable cracking reactions. The treatment of reformer feeds to remove sulfur components is a well known method of maintaining process efficiency and protecting catalyst stability.

In the case of a hydrocarbon conversion process utilizing a regenerable zeolite-containing catalyst, it is well known that regeneration procedures which expose a zeolite-containing catalyst to steam severely effects the performance of the zeolite catalyst following regeneration. This performance loss, observed even under mild regeneration conditions, is typically not totally recoverable. Therefore, processes and methods to suppress zeolite activity loss in a hydrocarbon conversion process employing a regenerable zeolite are quite important in extending the useful life and thus the economic viability of such a process.

It has now been surprisingly found that if a hydrocarbon feed is first treated to reduce its fluoride content to below 100 ppb that the use of such a hydrocarbon feed in a hydrocarbon conversion process utilizing a regenerable zeolite will result in a higher retention of catalyst activity of the regenerated catalyst. The improvement being longer catalyst life expectancy because of the zeolite-containing catalysts greater resistance to activity loss during catalyst regeneration.

OBJECTS AND EMBODIMENTS

In another embodiment, a hydrocarbon conversion process is provided which utilizes the steps of: (a) subjecting a $C_1$–$C_{10}$ hydrocarbon feed to a fluorine compound removal step to reduce the feed fluorine content to below 100 ppb; (b) catalytically converting the fluorine-deficient $C_1$–$C_{10}$ hydrocarbon feedstock in the presence of a regenerable crystalline zeolite-containing hydrocarbon conversion catalyst where the crystalline zeolite has a silica to alumina ratio greater than 2; and, (c) regenerating the crystalline zeolite-containing hydrocarbon conversion which has become deactivated by the deposition of carbon in the form of coke upon the catalyst by exposing the deactivated catalyst to an oxygen-containing gas stream at conditions sufficient to combust the coke and restore catalyst activity. The process described above is useful in the conversion of $C_1$ to $C_{10}$ aliphatic hydrocarbon containing feedstocks in hydrocarbon conversion processes such as paraffin dehydrogenation, oligomerization, alkylation, aromatization, dehydrocyclodimerization, and the like.

In a preferred embodiment, the present invention is directed to an improved process for the dehydrocyclodimerization of a hydrocarbon feedstock comprising $C_2$ to $C_6$ aliphatic components in the presence of a regenerable ZSM-type zeolite catalyst. The hydrocarbon feedstock initially undergoes a fluorine compound removal step to reduce the concentration of fluorine in the feed to below 100 ppb. The feedstock thusly treated is catalytically dehydrocyclodimerized in the presence of a regenerable dehydrocyclodimerization catalyst comprised of a ZSM-type crystalline zeolite. When deactivated by the accumulation of carbonaceous deposits known as coke on the catalyst, the catalyst is regenerated by exposing it to an oxygen-containing gas at conditions sufficient to combust the coke on the catalyst. Besides comprising a ZSM-type zeolite component, the dehydrocyclodimerization catalyst preferably comprises a gallium component, a phosphorus-containing alumina component, and a refractory inorganic oxide component.

INFORMATION DISCLOSURE

The use of a crystalline zeolite in the catalysis of a hydrocarbon reaction is well known in the prior art. However, the improvement in stability of a regenerable zeolite-containing catalyst when processing a fluorine-deficient feed has not been fully recognized.

Methods for the removal of specific undesirable components from hydrocarbon feeds prior to or following hydrocarbon conversion process are well known. The removal of selected components from a gas stream by adsorption is shown in U.S. Pat. No. 2,180,712. The increased selectivity and surface area of molecular sieves has caused them to predominate in the removal of inorganic compounds from vapor streams. In Chapter 16 of *The Chemical Engineer's Handbook*, 5th Edition, McGraw-Hill Book Co., New York, 1973, the suitability of using alumina for drying gases and the defluorination of alkylates is indicated on Page 16-5. The use of fixed-bed, continuous, and continuous countercurrent gas and liquid sorption operations are described starting at Page 16-23. Examples are presented using moving or fluidized beds of activated charcoal and silica gel for gas treating operations. U.S. Pat. No. 3,775,310 presents a continuous ion exchange process using countercurrent flow of the adsorbent and treated liquid. The removal of fluoride compounds specifically to increase zeolite-containing hydrocarbon conversion catalyst stability is however not believed to be disclosed in any of these references.

U.S. Pat. No. 4,456,527 describes a hydrocarbon conversion process which utilizes a hydrotreating step to reduce the sulfur content of a feed to a catalytic reforming process. The sulfur content of the feed is reduced to protect the stability of a catalyst comprising a large pore type zeolite containing at least one Group VIII type metal. The intent of the '527 patent is to protect and maintain the stability of a zeolite-containing hydrocarbon conversion process. However, the '527 patent discloses the advantages of feed sulfur removal and is completely silent to the advantages of feed fluoride removal.

Surprisingly, many prior art patents disclose the use of a fluoride component to modify different properties of a zeolite in a zeolite-containing hydrocarbon conversion catalyst. U.S. Pat. No. 3,594,331 discloses a method for increasing the thermal stability of crystalline zeolites by treating the zeolite with a dilute solution of a fluorine compound. The treatment with a fluorine compound is a fluoride treatment (column 3, line 41 et. seq.). After the fluoride treatment has been completed, the zeolite (fluoride treated) incorporates 2 to 15 grams of fluoride per 10,000 grams of zeolite. The patent does note however that excess fluoride actually decreases the thermal stability of the zeolite.

U.S. Pat. No. 3,933,983 discloses a fluoride treatment process similar to U.S. Pat. No. 3,594,331 except that an ion exchange step is added (see claim 1). Additionally, the removal of fluoride-containing components within a zeolite with a soluble aluminum compound is disclosed in Canadian Patent No. 1,218,348. The removal of fluoride components is described as being desirable since the presence of such insoluble fluoride compounds in physical admixture with the aluminosilicate generally increases the rate of degradation of the aluminosilicates due to fluoride attack on the zeolite's lattice. Such fluorides have a tendency to cause fluxing of inorganic materials under thermal or hydrothermal conditions which may destroy the zeolites structure. The prior art disclosures mentioned immediately above emphasize the fact that fluoride has been used advantageously to modify catalyst properties during manufacture. The process of the instant invention, unlike that of the '348 Canadian patent, treats fluorides in the hydrocarbon feed by extracting them as opposed to removing fluorides in a catalyst as a result of catalyst manufacture.

Zeolite-containing catalyst regeneration methods are also well known in the prior art. Typically, the regeneration methods emphasize the importance of performing the zeolite catalyst regeneration procedure at low levels of moisture to reduce steam deactivation of the zeolite during regeneration procedures. Examples of such processes and methods include removing combustion moisture with a water-lean adsorbent as is done in U.S. Pat. No. 3,756,961, or by removing a portion of water containing gas from the system as is described in U.S. Pat. No. 4,480,144. Many other methods of regenerating zeolite catalyst to prevent thermal degradation of the zeolite by steam are disclosed. None have disclosed the advantages of regenerating a zeolite-containing catalyst accrued by processing only hydrocarbon feed containing less than 100 ppb fluoride.

The prior art discloses various aspects of the instant invention such as fluoride removal methods, zeolite catalyst treating methods and catalyst regeneration methods. However, no prior art disclosure describes a hydrocarbon conversion process such as described herein where a regenerable zeolitic catalyst's stability is improved by reacting it with hydrocarbon feeds which have been treated so they contain only minute amounts of fluorides.

DESCRIPTION OF THE DRAWING

The drawing presents $C_3$ feed conversion results of pilot plant testing performed on fresh and regenerated dehydrocyclodimerization catalysts as a function of hours-on-stream. The testing was performed using hydrocarbon feedstocks containing 13,000 ppb, 500 ppb, and 0 ppb levels of fluorine in the feed on zeolite-containing catalysts over a number of regeneration cycles.

DETAILED DESCRIPTION

In its broadest aspect, the present invention consists of reacting a hydrocarbon containing feedstock of exceedingly low fluorine content (less than 100 ppb) over a zeolite-containing hydrocarbon conversion catalyst where the zeolite-containing catalyst is regenerable. It has been found, surprisingly and unexpectedly, that a zeolite catalyst employed in the instant process exhibits a higher level of activity upon regeneration than a zeolite catalyst of the prior art. This results in a catalytic process with a longer catalyst life expectancy. This improved retention of catalytic activity after one or more regeneration procedures increases the attractiveness of such a process by allowing the catalyst of the instant invention to be regenerated more times before zeolite catalyst replacement is required.

In accordance with the present invention, the process disclosed herein involves in part a hydrocarbon feed pretreatment step to reduce the level of fluoride components in a hydrocarbon feedstock to below 500 ppb, and preferably to below 100 ppb based upon the weight of elemental fluorine in the treated hydrocarbon. The hydrocarbon is pretreated before it is exposed to a regenerable zeolite-containing hydrocarbon conversion catalyst at hydrocarbon conversion conditions.

The terms "fluoride", "fluoride component", and/or "fluoride-containing" are used herein to describe any chemical formulation containing elemental fluorine alone or within its molecular structure. This includes fluorine in its elemental and diatomic form and compounds containing fluorine atoms and atoms of other elements. The hydrocarbon-containing process streams from which these materials are removed may be characterized as fluid streams as they may be both gaseous and liquid. In a refinery situation, it is anticipated that fluoride-containing components may originate from fluoride-containing catalysts such as boron trifluoride or aluminum fluoride, hydrogen fluoride, and the like, from a reactant used in a fluorination step, or from by-products of a hydrogen conversion reaction such as alkylfluorides produced as a by-product of an HF alkylation reaction. The previous description of potential sources of and types of fluoride components in the hydrocarbon feed of the present invention is not meant to restrict the instant process. It is anticipated that hydrocarbon feedstocks can become contaminated with fluoride components in a refinery in a myriad of methods. The method that a feedstock may become contaminated is not as important to this invention as is the treatment and processing of such a contaminated feedstock.

A variety of methods are known in the art to remove fluoride components from gaseous and liquid hydrocarbon streams. One of the most common methods of removing these fluoride-containing chemicals is to pass the fluid stream through a bed of selective adsorbent such as alumina, bauxite, silica gel, or activated charcoal. This is normally accomplished using a fixed bed of the adsorbent, but moving beds have also been utilized. For instance, alumina is used to remove alkylfluorides from a liquid hydrocarbon stream. Such fixed bed adsorbent systems are commonly referred to as "guard beds" as their purpose as a fixed "bed" of adsorbent is to "guard" a reactor full of expensive catalyst from being contaminated with a catalyst deactivator such as sulfur or, as in this case, fluoride components. It is anticipated that guard beds that are useful in removing fluorides from hydrocarbon feedstocks of the present invention could contain any compound, in solid, gel, or liquid that is known to scavenge fluoride compounds. It is also anticipated that such a guard bed could manifest itself in any useful flowscheme known in the prior art. As mentioned above, some useful adsorbents including alumina, activated charcoal, and silica gel are all known to be useful guard bed adsorbents. In addition, zeolites, amorphous silica aluminas, crystalline silica, and the like could all be usefully utilized in the instant process. It is anticipated that for ease of operation, a guard bed system would consist of two parallel guard bed vessels, each containing a similar fluoride adsorptive material. Having two guard bed vessels will enable one guard bed vessel to be in operation while the other is not. In this way, a continuous process can be maintained. It is also possible that distinct beds of two or more adsorbents or intimate mixtures of two or more fluoride-scavenging adsorbents can be utilized in a fluoride guard bed of the instant invention. Methods of using liquids to remove halogen components, including fluoride components from hydrocarbon feeds are also well known and documented. A basic aqueous solution works well in removing most halogen-containing chemicals. U.S. Pat. No. 3,917,733 describes a continuous process for treating a gaseous and a liquid halogen-containing hydrocarbon stream simultaneously and continuously to reduce said halogen content of the hydrocarbon streams to low levels. The treatment described in the '733 patent is accomplished with alumina which becomes spent and is replaced on a continuous basis. Such a process also is capable of employing other fluoride-scavenging adsorbents besides alumina. A continuous process as described in the '733 patent or similar, or other continuous adsorbent processes known in the prior art would be particularly advantageous as the fluoride removal step of the instant process as a continuous fluoride removal step would result in a more efficient overall process.

The above description of fluoride removal process which can be employed to remove fluorides from the hydrocarbon feed of the instant process has been broad and brief. It is anticipated that any process utilizing an adsorbent, liquid, or some other known method to remove fluoride or fluoride-containing components from a gaseous or liquid hydrocarbon feed may be successfully employed as a portion of the instant process. In fact, it is anticipated that a two-bed zeolite catalyst containing hydrocarbon conversion process could be successfully employed to remove fluorides from a fluoride-containing hydrocarbon feed. Such a process would utilize the crystalline aluminosilicate zeolite in the first reactor as a sacrificial catalyst bed. The first reactor products could be separated to recover reactants or sent in entirety to a second or subsequent reactor containing a crystalline aluminosilicate catalyst for further processing. The type of process would be characterized in that the fluoride content of the feed would be reduced to below 100 ppb in the first zeolite catalyst containing reactor and processed in subsequent zeolite catalyst containing reactors. Whatever process is employed to remove fluorides from a fluoride-containing hydrocarbon feed must however be capable of reducing the fluoride content of the said hydrocarbon to below 500 ppb and preferably to a level below 100 ppb.

The fluoride removal step can be useful on any hydrocarbon feeds containing more than 100 ppb fluorides. However, due to the erection and operational costs of a fluoride removal system, it is anticipated that such a system will be most useful for removing fluorides from fluoride-containing hydrocarbon feeds containing greater than 500 ppb fluorides.

The hydrocarbon conversion process disclosed as the process of the present invention comprises all hydrocarbon conversion processes which employ a regenerable zeolite-containing catalyst to accomplish a desired hydrocarbon conversion reaction. Examples of such hydrocarbon conversion processes which have been disclosed as employing a regenerable zeolite-containing catalyst include among others, catalytic cracking, catalytic reforming, catalytic hydrotreating, alkylation of aromatic and aliphatic hydrocarbons, dehydrocyclodimerization, oligomerization, dehydrogenation, and so forth. It is anticipated that the desired hydrocarbon conversion reaction can take place in the presence of a regenerable zeolite-containing catalyst in a reactor system comprising a fixed bed system, a moving bed system, a fluidized bed system, or in a batch-type operation; however, in view of the fact that attrition losses of the valuable regenerable zeolite-containing catalyst should be minimized and of the well-known operation advantages, it is preferred to use either a fixed bed catalytic system, or a dense phase moving bed system such as is shown in U.S. Pat. No. 3,725,249. It is also anticipated that the catalytic system may comprise a single regenerable catalyst which has been formulated with a zeolite or a mixture of two or more unique regenerable catalysts of which at least one has been formulated with a zeolite component.

The zeolite component of the regenerable zeolite-containing hydrocarbon conversion catalyst may be any natural or synthetic zeolite known. Zeolitic materials are typically ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Zeolites may be represented by the empirical formula:

$MnO_{2/n} \cdot Al_2O_3 \cdot xSiO_2 \cdot yH_2O$ in which n is the valence of M which is generally an element of Group I or II, in particular, sodium, potassium, magnesium, calcium, strontium, or barium and x is generally equal to or greater than 2.

Prior art techniques have resulted in the formation of a great variety of synthetic zeolites. The zeolites have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,110,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), zeolite ZSM-35 (U.S. Pat. No. 4,016,245), zeolite ZSM-38 (U.S. Pat. No. 4,046,859), and zeolite ZSM-23 (U.S. Pat. No. 4,076,842), to name but a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to infinity. U.S. Pat. No. 3,941,871 (No. Re. 29,948) discloses a porous crystalline silicate made from a reaction mixture containing no deliberately added alumina in the recipe and exhibiting the X-ray diffraction pattern characteristic of ZSM-5 type zeolites. U.S. Pat. Nos. 4,061,724, 4,073,865, and 4,104,294 describe crystalline silicates or organosilicates of varying alumina and metal content.

In a preferred embodiment, the zeolite-containing catalyst of the present invention exhibits a silicon to alumina molar ratio of 2 or more. The zeolites disclosed hereinabove as well as other known synthetic and naturally occurring zeolites which have a silicon to alumina molar ratio greater than 2 are all candidates as the preferred zeolitic component of the regenerable zeolite-containing hydrocarbon conversion catalyst of the instant invention.

It is an important aspect of the instant invention that the zeolite-containing hydrocarbon conversion catalyst be regenerable by the oxidation or burning of catalyst deactivating carbonaceous deposits with oxygen or an oxygen-containing gas. By "regenerable", it is meant that at least a portion of the zeolite-containing catalyst's initial activity can be recovered by combusting the coke deposits on the catalyst with oxygen or an oxygen-containing gas. The prior art is replete with zeolite catalyst regeneration techniques. Some of these regeneration techniques involve chemical methods of increasing the activity of deactivated zeolites. Others are related to processes or methods for regenerating carbon (also known as coke) deactivated zeolites by combustion of the coke with an oxygen-containing gas stream. For example, U.S. Pat. No. 2,391,327 (Mekler) discloses the regeneration of catalysts contaminated with carbonaceous deposits with a cyclic flow of regeneration gases. U.S. Pat. No. 3,755,961 relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieves. U.S. Pat. No. 4,480,144 relates to the use of a circulating gas to regenerate a coke deactivated zeolite-containing catalyst. The circulating gas is maintained at a low moisture level by purging wet gases from the loop while simultaneously introducing dry gases to the loop. The conditions and methods at which a zeolite-containing catalyst may be regenerated by coke combustion with oxygen vary. It is typically desired to perform the coke combustion at conditions of temperature, pressure, gas space velocity, etc. which are least damaging thermally to the catalyst being regenerated. It is also desired to perform the regeneration in a timely manner to reduce process down-time in the case of a fixed bed reactor system or equipment size in the case of a continuous regeneration process.

Optimum regeneration conditions and methods are those typically disclosed in the prior art as mentioned hereinbefore. To reiterate, zeolite regeneration is typically accomplished at conditions including a temperature range of from 315° C. to 500° C. or higher, a pressure range of from atmospheric to 20 atmospheres, and a regeneration gas oxygen content of from 0.1 to 23.0 mole percent. The oxygen content of the regeneration gas is typically increased during the course of a catalyst regeneration procedure based on catalyst bed outlet temperatures in order to regenerate the catalyst as quickly as possible while avoiding catalyst-damaging process conditions.

The regeneration of zeolite catalysts is preferably conducted in two steps, a main burn and a clean-up burn. The main burn constitutes the principal portion of the regeneration process. With the molecular oxygen level maintained below about 1.0 mole percent during this main burn, the burning of the coke consumes a major portion of the oxygen so that molecular oxygen in amounts less than that found at the reactor inlet is detected in the gaseous stream at the outlet of the reactor vessel. Near the end of the main burn, oxygen consumption across the catalyst bed will start to decrease producing an increasing concentration of molecular oxygen at the exit of the reactor. This point in the main burn is referred to as the oxygen breakthrough and essentially marks the end of the main burn. At this point, the clean-up burn portion of the regeneration is initiated by gradually increasing the molecular oxygen concentration in the gas introduced to the catalyst bed. The oxygen concentration can usually be slowly increased to about 7.0 mole percent or greater until the end of the clean-up burn which is indicated by a gradual decline in the temperature at the exit of the catalyst bed until the inlet and outlet temperatures of the catalyst bed merge, i.e. there is essentially no temperature rise across the bed.

U.S. Pat. No. 4,645,751 discloses a specific method of regenerating a noble metal containing zeolite catalyst. The method disclosed involves a first coke-burning step followed by a second noble metal redispersing step. It is anticipated that reactivation techniques such as the noble metal redispersing technique taught in the '751 patent may be an aspect of the regeneration technique utilized in the practice of the present invention. Such reactivation techniques are utilized to restore catalytic activity beyond that gained through zeolite catalyst coke combustion methods alone. Another example of zeolitic catalyst activity reactivation techniques disclosed in the prior art is found in U.S. Pat. No. 4,649,127 which describes the use of a hydrogen contacting step followed by a polar solvent contacting to reactivate nitrogen poisoned catalysts. The regenerable zeolite hydrocarbon conversion catalyst utilized in the instant invention must exhibit catalyst activity recovery following a coke burning regeneration step. In addition to the coke burning step, other methods of zeolite reactivation known in the prior art may be employed in the regeneration of the zeolite-containing catalyst of the present invention to further enhance the activity of the regenerated catalyst.

It is a preferred embodiment of the hydrocarbon conversion process of the present invention that the hydrocarbon feedstock employed in the process is comprised of $C_1$-$C_{10}$ aliphatic and aromatic hydrocarbons. The hydrocarbon feedstock may contain minor amounts of larger carbon number hydrocarbons and/or hydrocarbon feedstock diluents such as, but not limited to, hydrogen, nitrogen, oxygen, carbon dioxide, steam, and so forth. It is also an aspect of the preferred process that the $C_1$-$C_{10}$ aliphatic and aromatic hydrocarbon feedstock may comprise a pure component selected from the $C_1$-$C_{10}$ aliphatic and aromatic hydrocarbons, a mixture of two pure components such as ethane and ethylene and so forth up to and including a feedstock containing a mixture of many to all $C_1$-$C_{10}$ aliphatic and aromatic hydrocarbons. That is to say, a $C_1$-$C_{10}$ aliphatic and aromatic hydrocarbon feedstock may contain one or more $C_1$-$C_{10}$ aliphatic and aromatic hydrocarbon components. $C_1$-$C_{10}$ aliphatic and aromatic hydrocarbons were chosen as the preferred feedstock for the instant process for a variety of reasons. It was felt that $C_1$-$C_{10}$ hydrocarbons were the most likely to contain deleterious amounts of fluoride components in the form of alkylfluorides. It was also felt that processes employing such $C_1$-$C_{10}$ hydrocarbon feedstocks such as catalytic reforming, dehydrocyclodimerization, hydrogenation, and the like are typically operated at reaction conditions which can cause zeolite-containing catalysts to deactivate quickly by coke accumulation thereon resulting in frequent catalyst regeneration requirements. Therefore, the process of this invention is particularly suited to extending the viability of regenerable zeolite catalysts employed in hydrocarbon conversion processes utilizing a $C_1$-$C_{10}$ aliphatic and aromatic hydrocarbon feedstock.

In preferred embodiments of the present invention, the desired hydrocarbon conversion processes of the present invention are dehydrogenation, oligomerization, alkylation, and dehydrocyclodimerization.

Dehydrogenation is a well-known hydrocarbon conversion process. Dehydrogenation may be effected by reacting dehydrogenatable hydrocarbons in a dehydrogenation process at dehydrogenation conditions in the presence of certain zeolite-containing catalytic compositions of matter. The particular dehydrogenation catalysts which are employed are well known in the art and comprise such compounds as nickel, and iron, and the like composited on a solid zeolite-containing support. Some dehydrogenation processes have employed, in addition to the dehydrogenation catalysts, an oxidation catalyst in the reaction process. The presence of the oxidation catalyst is precipitated by the fact that it is advantageous to oxidize the hydrogen which is produced by contact with an oxygen-containing gas in order to maintain the desired reaction temperature and reaction equilibrium. For example, styrene, which is an important chemical compound utilized for the preparation of polystyrene, plastics, resins or synthetic elastomers such as styrene-butadiene rubber, etc., may be prepared from the dehydrogenation of ethylbenzene. A variety of dehydrogenatable hydrocarbons are also $C_1$-$C_{10}$ aliphatic and aromatic hydrocarbons. Examples of such hydrocarbons which are susceptible to dehydrogenation in a dehydrogenation process utilizing known zeolite-containing dehydrogenation catalysts include lower alkyl-substituted aromatic hydrocarbons such as ethylbenzene, diethylbenzene, isopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnaphthalene, diethylnaphthalene, etc.; paraffins such as ethane, propane, n-butane, isobutane, n-pentane, isopentane, n-hexane, n-heptane, n-octane, n-nonane, n-decane, and branched chain isomers thereof; cycloparaffins such as cyclobutane, cyclopentane, cyclohexane, methylcyclopentane, methylcyclohexane, ethylcyclopentane; olefins such as ethylene, propylene, 1-butene, 2-butene, 1-pentene, 2-pentene, 1-hexene, 2-hexene, 3-hexene, and branched chain derivatives thereof, etc. It is intended to include any zeolite-containing dehydrogenation catalyst disclosed in the prior art as a regenerable zeolite-containing catalyst of a preferred dehydrogenation conversion process of the present invention. The dehydrogenation of dehydrogenatable hydrocarbons such as, for example, ethylbenzene, propane, or ethane is effected by contacting the desired dehydrogenatable hydrocarbon with the aforesaid regenerable zeolitecontaining hydrocarbon conversion catalyst. Dehydrogenation conversion conditions typically are in the range of from 350° C. to about 750° C. and at reaction pressures ranging from about 0.1 to about 20 atmospheres. The exact dehydrogenation conditions are, however, a function of the particular hydrocarbon undergoing dehydrogenation. Other reaction conditions will include a Liquid Hourly Space Velocity based on the hydrocarbon charge of from about 0.1 to about 20 $hr^{-1}$. Diluents such as steam, hydrogen, oxygen, nitrogen, and the like may be added to the feed or at any point in the reactor. The number of reactors or catalyst beds utilized in the dehydrogenation reaction zone may be one or more than one, and as previously mentioned, the dehydrogenation catalyst may be employed in conjunction with an oxidation catalyst to increase process efficiency. The above description of dehydrogenation processing conditions and methods is meant to be exemplary in nature and is not meant to restrict the possible dehydrogenation process schemes able to be practiced within the scope of this invention.

A second preferred hydrocarbon conversion process of the instant invention is oligomerization. The oligomerization process is well known in the prior art. In a brief description, the oligomerization process comprises uniting hydrocarbon olefins into larger olefinic hydrocarbon molecules consisting of multiples of the original molecules. Therefore, the oligomerization of, for example, ethylene ($C_2=$) would produce $C_4$, $C_6$, and perhaps $C_8$ olefins or dimers, trimers, and tetramers of the original ethylene feed molecule. In the case of a mixed light olefin feed, combinations of dimers, trimers, and perhaps tetramers and more highly substituted molecules comprising a mixture of the mixed feed olefins would be produced. In general, the feedstock to an oligomerization reactor might comprise one or a mixture of two or more olefins containing from 2 to 10 carbon atoms, and preferably containing from 2 to about 6 carbon atoms such as ethylene, propylene, butene-1, butene-2, pentene-1, pentene-2, and pentene-3. Oligomerization may then be effected by reacting the olefin in the presence of a zeolite-containing catalyst at oligomerization conditions which includes a temperature in the range of from about −20° C. to about 120° C., the preferred range being from about 30° C. to about 80° C., and a pressure in the range of from about 5 to about 68 atmospheres. The pressure which is utilized may be the autogenous pressure provided for by the feedstock, if in gaseous phase, or, the feedstock may supply only a partial pressure, the remainder of such pressure being provided by the introduction of an inert gas such as nitrogen, helium, argon, etc. into the reaction zone. As stated hereinabove, the products of the oligomerization reaction comprise mainly dimers, trimers, and tetramers of the original olefinic reactant or reactants. Such oligomerization products are useful in further processing such as in the production of linear alkylbenzenes, and as a motor fuel constituent among other uses. It is of course an important aspect of the present invention that the oligomerization reaction take place in the presence of a regenerable zeolite-containing catalyst utilizing a feed that has been pretreated to reduce the fluoride content therein to below 100 ppb. It is also an aspect of the preferred oligomerization process that the zeolite have a silicon to aluminum molar ratio of 2 or more and that the zeolite-containing catalyst is regenerable by combustion of coke thereon with an oxygen-containing gas at regeneration conditions.

Alkylation is a third preferred hydrocarbon conversion process of the instant invention. Motor fuel alkylation and aromatic alkylation utilizing a zeolite catalyst comprise some of the various types of alkylation processes which can be accomplished utilizing a $C_1$–$C_{10}$ aliphatic and aromatic hydrocarbon feedstock which has been first treated to reduce the fluoride content therein to less than 100 ppb. Motor fuel alkylation is achieved as a result of the reaction between an isoparaffin and an olefin. The motor fuel alkylate product is particularly useful as a high octane blending stock in gasoline. The use of a crystalline aluminosilicate was disclosed in U.S. Pat. No. 3,251,902 among others as an effective motor fuel alkylation catalyst. The alkylation of aromatics such as benzene with olefins such as ethylene, propylene, and so forth is also well known in the prior art for producing such useful aromatic products as ethylbenzene and cumene to mention but a few. Such products are useful as plastic precursors, as feedstock for other petrochemical processes and so forth. Processing schemes and conditions useful in various alkylation reactions vary widely depending upon feedstock, catalyst, whether the reaction is gas phase or liquid phase, and so on. The use of a zeolite-containing regenerable alkylation catalyst in a process for the alkylation of an olefin with a paraffin while not common is disclosed in the prior art such as in U.S. Pat. No. 3,778,489. Conditions suitable for the alkylation of such a feedstock in the presence of a zeolite-containing catalyst include a temperature of from −60° C. to 100° C., a pressure of from 1 to 20 atmospheres, an olefin to paraffin molar feed ratio of from 1:1 to 1:20, and a liquid hourly space velocity of from 0.1 to 20.

The use of zeolite-containing catalysts in the alkylation of aromatic hydrocarbons is well known and documented such as in U.S. Pat. No. 4,185,040 which describes a crystalline aluminosilicate zeolite catalyst and its usefulness in the alkylation of an aromatic with a $C_2$–$C_4$ olefin. Process conditions sufficient to promote the alkylation of an aromatic such as benzene with a $C_2$–$C_4$ olefin in the presence of a regenerable zeolite-containing catalyst include a temperature of from 80° C. to 400° C., a pressure of from 1 to 40 atmospheres, an aromatic to olefin mole ratio of from 1:1 to 20:1, and a liquid hourly space velocity of from 0.1 to 20. Process flow schemes, process combinations, the use of cofeeds, etc. are all applicable to the aromatic alkylation conversion process of the present invention. It is therefore an aspect of the preferred alkylation conversion process of the instant invention that the alkylation reaction be performed at any conditions and using any method disclosed in the prior art which utilizes a regenerable zeolite-containing catalyst.

Dehydrocyclodimerization is the final preferred process of the present invention. Dehydrocyclodimerization is a process utilizing reactants comprising paraffins and olefins, containing from 2 to 6 carbon atoms per molecule. These reactants are reacted over a catalyst to produce primarily aromatics, $H_2$ and light ends as byproducts. Typically, the dehydrocyclodimerization reaction is carried out at temperatures in excess of 260° C. using dual functional catalysts containing acidic and dehydrogenation components. These catalysts include crystalline aluminosilicate zeolites which have been successfully employed as catalyst components for the dehydrocyclodimerization reaction.

Many regenerable zeolite-containing catalysts have been disclosed in the prior art as useful for the dehydrocyclodimerization of $C_2$–$C_6$ aliphatic hydrocarbons. These catalysts as well as processes employing such catalysts are disclosed as potential catalysts and processing schemes of the preferred dehydrocyclodimerization process of the present invention.

It is most preferred that the hydrocarbon conversion process of the instant invention comprise first subjecting a $C_2$–$C_6$ aliphatic hydrocarbon feedstock to a fluoride removal step to reduce the concentration of fluoride in said feed to below 100 ppb. The treated feed is then contacted with a ZSM-type zeolite-containing catalyst in a dehydrocyclodimerization reaction zone at dehydrocyclodimerization conditions followed by regeneration of the coke deactivated zeolite catalyst in the presence of an oxygen-containing gas. The ZSM zeolite component of the preferred dehydrocyclodimerization catalyst is preferably ZSM-5. The dehydrocyclodimerization catalyst preferably contains, in addition to a ZSM-5 zeolite component, from 0.1 to 5 wt. % of a gallium component, and from 30 to 70 wt. % of a phosphorus-containing alumina component. It is also preferred that the phosphorus to alumina ratio of the phosphorus-containing alumina ranges from 1:1 to 1:100. U.S. Pat. No. 4,636,483 describes the preferred dehydrocyclodimerization catalyst and is incorporated herein by reference.

It has not been intended through the description of the four preferred hydrocarbon conversion processes hereinabove to limit the hydrocarbon conversion aspect of the process of the present invention. As previously stated, the instant process will be useful in hydrocarbon conversion processes which utilize a regenerable zeolite to maintain regenerated zeolite-containing catalyst activity by first treating said hydrocarbon feed to reduce the fluoride content therein to below 500 ppb and preferably below 100 ppb. Additionally, it is not intended to limit the scope of the preferred hydrocarbon conversion processes useful in the instant process by the generic description of said processes given above. The only limitation placed on said processes is that the feedstock useful in such preferred processes must be limited at most to $C_1$–$C_{10}$ aliphatic and aromatic hydrocarbons, that catalysts useful in said processes must be regenerable by coke combustion and that the catalyst must contain a zeolite with a silicon to alumina molar ratio greater than 2. It is left up to the prior art to limit the scope of hydrocarbon conversion processes useful in the instant invention based upon the limitations set forth herein.

It is an aspect of this invention that the hydrocarbon conversion process be a complete process. That is to say, the hydrocarbon conversion process will comprise a reaction section and other sections such as gas recycle, liquid recycle, product recovery, and the like such that the process is viable and efficient. Examples of some of the product recovery techniques that could be employed alone or in combination in the product recovery zone of a hydrocarbon conversion process are: distillation including vacuum, atmospheric, and superatmospheric distillation; extraction techniques including, for example, liquid/liquid extractions, vapor/liquid extractions, supercritical extractions and others; absorption techniques, adsorption techniques, and any other known mass transfer techniques which can achieve the recovery of the desired products.

The following examples will serve to illustrate certain specific embodiments of the herein disclosed invention. The examples should not, however, be construed as limiting the scope of the invention as set forth in the claims as there are many variations which may be made thereon without departing from the spirit of the invention, as those of skill in the art will recognize.

EXAMPLE I

This example introduces methods used for preparing and/or determining the fluoride content of fluoride-containing light hydrocarbon feedstocks. Three propane feedstocks prepared and/or evaluated utilizing the method as set forth herein below were subsequently tested in Example II.

The first propane feedstock was analyzed directly and determined to contain 13 ppm (13,000 ppb) fluoride therein. A spectrophotometric analysis was used to determine the propane fluoride content. The method used consisted of first burning a known weight of propane feed with a stainless steel burner in a Wickbold quartz-tube oxy-hydrogen combustion apparatus. The combustion products were absorbed in a 25 ml solution of 2% boric acid that had been subsequently diluted with water from an apparatus cleaning step. The solution was then treated with 5 ml of formaldehyde to remove excess peroxides and heated until 70 ml of solution remain. The 70 ml of fluoride-containing solution was then diluted to 100 ml. It was necessary to determine the proper aliquot empirically from a dilution of the diluted absorber solution containing no fluoride reagent. 40 ml of water and 10 ml of a fluoride reagent prepared by mixing equal volumes of a solution of 2.87 g SPADNS Eastman Kodak 7309 (4-5-dihydroxy-3-(p-sulfophenylazo)-2,7-naphthalene-disulfonic acid, trisodium salt) in 500 ml water and a zirconyl chloride solution comprising 0.133 g zirconyl chloride, 350 ml conc HCl diluted to 500 ml were added to a 100-ml volumetric flask. Using a Mohr pipet, 0.2 ml of the diluted absorber solution was transferred to the flask containing water and fluoride reagent and the degree of bleaching of the fluoride reagent was noted. Diluted absorber solution was added to the reagent flask in 0.2 ml increments until a suitable degree of bleaching was obtained. The final solution was diluted to the 100 ml mark with water, mixed well, and the fluoride concentration was determined from a prepared calibration curve based upon the volume of absorber solution used.

The fluoride contents of the propane feeds containing 500 ppb and essentially 0 ppb fluorides were determined in a different manner. In both cases, the propane feed was pretreated by passing the feed across a guard bed containing a gamma-alumina adsorbent at 230° C. and at from 13.6 to 17.0 atmospheres. The guard bed was replaced and the alumina analyzed for fluorides until, in the case of the second feedstock, a trace of fluoride was found on the guard bed alumina and, in the case of the third feedstock, no fluorides were detected on the alumina. The second and third feedstocks were then processed in the pilot plant per the procedure established in Example II and a representative sample of the spent catalyst from Example II was then analyzed for fluoride. From the spent catalyst fluoride analysis, and based upon the weight of feed processed, it was determined that the feedstock prepared for the second series of tests contained at least 500 ppb fluoride and the feedstock prepared for the third series of tests was essentially fluoride-free.

EXAMPLE II

In order to demonstrate the retention of catalytic activity of a regenerable zeolite-containing catalyst when processing a feedstock containing less than 100 ppb of fluorine, a hydrocarbon conversion catalyst disclosed in U.S. Pat. No. 4,636,483 was prepared by the method set forth below. A first solution was prepared by adding phosphoric acid to an aqueous solution of hexamethylenetetramine (HMT) in an amount to yield a phosphorus content of the finished catalyst equal to about 11 wt. %. A second solution was prepared by adding a ZSM-5 type zeolite to enough alumina sol, prepared by digesting metallic aluminum in hydrochloric acid, to yield a zeolite content in the finished catalyst equal to about 67 wt. %. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres. These spheres were removed from the oil bath, water washed, air dried, and calcined at a temperature of about 482° C. A solution of gallium nitrate was utilized to impregnate the spheres to achieve a gallium content on the finished catalyst equal to about 1 wt. %. After impregnation, the spheres were calcined a second time, in the presence of steam, at a temperature of about 649° C.

The hydrocarbon conversion catalyst as prepared above was utilized in a dehydrocyclodimerization pilot plant to convert a propane feed into aromatics. Three series of tests were performed. Each series was performed with a feedstock containing different amounts of fluoride. Each cycle consisted of a pilot plant conversion run lasting about 100 hours, followed by a catalyst regeneration step. The amounts of fluorine in the feed were 13,000 ppb, 500 ppb, and essentially 0 ppb for series 1, 2, and 3, respectively. The zeolite-containing catalyst was exposed to the propane feedstock and tested for dehydrocyclodimerization performance in identically the same manner in all series and cycles using a flow reactor processing a feed comprising 100% propane and varying levels of fluoride. The operating conditions used in the performance test comprised a reactor pressure of 1 atmosphere, a liquid hourly space velocity of 0.8 hr$^{-1}$, and a reaction zone inlet temperature of about 538° C. The change in the conversion of the feed over 100 hours of processing was monitored.

Following each pilot plant run, the same catalyst was regenerated and rerun for approximately 100 hours while processing a feedstock with the same level of fluoride. This testing was repeated for four or five times for each test series, with each pilot plant run of the catalyst comprising one cycle in the series.

The catalyst regeneration method was similar in all cases. The procedure consisted of placing the coke deactivated zeolite-containing catalyst in a 0.28 meter (11-inch) bed and establishing an inert gas flow across the catalyst bed at a gas hourly space velocity of 4800 hr$^{-1}$. The corresponding superficial velocity was 0.5 m/sec (1.6 ft/sec) and the regeneration was performed at atmospheric pressure. The regeneration temperature and oxygen content were varied over the 7-hour regeneration based upon the schedule below:

| Hours | Temp. (°C.) | $O_2$, mole % |
|---|---|---|
| 0-1 | 490 | 1 |
| 1-2 | 490 | 2 |
| 2-3 | 490 | 5 |
| 3-4 | 490 | 20 |
| 4-5 | 490-540 | 20 |
| 5-7 | 540 | 20 |

After regeneration, the catalyst was cooled and then reloaded into the dehydrocyclodimerization pilot plant for another cycle of testing. Each cycle is counted upon the completion of a pilot plant run. Thus, the pilot plant testing of the fresh catalyst would be cycle number 1. A four-cycle catalyst will have undergone three regenerations.

The surprising pilot plant results of the series of tests can be found in the attached Figure. The Figure is a plot of $C_3$ conversion over time in the pilot plant. First and last cycle pilot plant conversion results are plotted for each of the series of three tests. Before discussing the results, it should be noted that the initial cycle results using a fresh catalyst in each of the three series were essentially identical. This result indicates that the pilot plant test results are reproducible. The first series utilized a $C_3$ feedstock containing 13 ppm of fluorine. After four cycles in which three catalyst regeneration steps had been performed, the catalyst lost 12% of its original $C_3$ conversion ability. The second series utilized a $C_3$ feedstock containing 500 ppb fluorine. After five cycles in which four catalyst regeneration steps had been performed, the catalyst lost about 6% of its original $C_3$ conversion ability. The final series, series 3, utilizing an essentially fluorine-free $C_3$ feed exhibited no loss of $C_3$ conversion over five cycles of testing including four regenerations.

It can be readily seen from these results that the removal of fluorine compounds from a hydrocarbon feedstock and the processing of such a feedstock containing very low levels of fluorine is highly desirable in maintaining the activity of a zeolite-containing regenerable hydrocarbon conversion catalyst. The presence of even small amounts (500 ppb) of fluorides caused appreciable catalyst activity loss after only four regenerations, thus providing the impetus for removing as much detrimental fluorides from the feed as possible.

What is claimed is:

1. A hydrocarbon conversion process comprising reducing the fluoride content of a fluoride-containing hydrocarbon feed to below 100 ppb and catalytically converting the hydrocarbon feed in the presence of a catalyst comprising a regenerable crystalline zeolite at hydrocarbon conversion conditions where the crystalline zeolite catalyst is regenerated by a procedure which comprises the combustion of carbonaceous material thereon with an oxygen-containing gas.

2. The hydrocarbon conversion process of claim 1 further characterized in that the crystalline zeolite catalyst has a silicon/aluminum molar ratio of 2 or more.

3. A hydrocarbon conversion process comprising the steps of:
 (a) subjecting a fluoride-containing hydrocarbon feed comprising $C_1$–$C_{10}$ hydrocarbons to a fluoride removal step and reducing the concentration of fluorine in said fluoride-containing hydrocarbon feed to below 100 ppb;
 (b) catalytically converting the hydrocarbon feed having a fluoride concentration of below 100 ppb in the presence of a regenerable hydrocarbon conversion catalyst comprising a crystalline zeolite with a silica/aluminum molar ratio of greater than 2; and,
 (c) regenerating the regenerable hydrocarbon conversion catalyst which has become deactivated by deposition of carbonaceous material thereon by a procedure which comprises exposing said deactivated catalyst to an oxygen-containing gas stream at regeneration conditions.

4. The hydrocarbon conversion process of claim 3 further characterized in that the conversion process is dehydrocyclodimerization.

5. A hydrocarbon conversion process comprising the steps of:
 (a) subjecting a hydrocarbon feed with a fluoride content greater than 500 ppb and comprising $C_1$–$C_6$ aliphatic hydrocarbons to a fluoride removal step to reduce the concentration of fluoride in said feed to below 100 ppb;
 (b) catalytically dehydrocyclodimerizing the aliphatic hydrocarbon feed having a fluoride concentration of below 100 ppb in the presence of a dehydrocyclodimerization catalyst comprising a crystalline zeolite, and recovering aromatic hydrocarbons; and
 (c) regenerating said zeolite-containing catalyst which has been deactivated by the deposition of carbonaceous material thereon by a procedure which comprises exposing said deactivated zeolite-containing catalyst to an oxygen-containing gas at catalyst regeneration conditions.

6. The hydrocarbon conversion process of claim 5 further characterized in that the zeolite component of the dehydrocyclodimerization catalyst is ZSM-5.

7. The hydrocarbon conversion process of claim 6 further characterized in that the dehydrocyclodimerization catalyst is comprised of from 0.1 to 5.0 wt. % of a gallium component.

8. The hydrocarbon conversion process of claim 7 further characterized in that the dehydrocyclodimerization catalyst is comprised of from 30 to 70 wt. % of a phosphorus-containing alumina.

9. The hydrocarbon conversion process of claim 8 further characterized in that the phosphorus to alumina ratio of the phosphorus containing alumina of the dehydrocyclodimerization catalyst ranges from 1:1 to 1:100.

10. The hydrocarbon conversion process of claim 5 further characterized in that the fluoride removal step comprises a guard bed containing a fluorine component absorptive compound.

11. The dehydrocyclodimerization process of claim 5 further characterized in that the fluoride removal step comprises the use of a non-regenerative adsorbent in a continuous process.

* * * * *